United States Patent
Zeika et al.

(10) Patent No.: US 8,057,712 B2
(45) Date of Patent: *Nov. 15, 2011

(54) RADIALENE COMPOUNDS AND THEIR USE

(75) Inventors: Olaf Zeika, New York, NY (US); Steffen Willmann, Dresden (DE); Sascha Dorok, Dresden (DE); Ansgar Werner, Dresden (DE); Christine Bachmann, Radebeul (DE)

(73) Assignee: Novaled AG, Dresden (DE)

( * ) Notice: Subject to any disclaimer, the term of this patent is extended or adjusted under 35 U.S.C. 154(b) by 155 days.

This patent is subject to a terminal disclaimer.

(21) Appl. No.: 12/264,511

(22) Filed: Nov. 4, 2008

(65) Prior Publication Data

US 2010/0102709 A1 Apr. 29, 2010

Related U.S. Application Data

(63) Continuation-in-part of application No. 12/111,326, filed on Apr. 29, 2008, now Pat. No. 7,981,324.

(60) Provisional application No. 61/107,826, filed on Oct. 23, 2008.

(51) Int. Cl.
H01B 1/12 (2006.01)
H01J 1/62 (2006.01)
C07C 255/45 (2006.01)

(52) U.S. Cl. .................. 252/519.21; 252/500; 313/504; 558/434; 558/430; 546/330

(58) Field of Classification Search ............. 252/519.21, 252/500; 313/504; 558/434, 430; 546/330
See application file for complete search history.

(56) References Cited

U.S. PATENT DOCUMENTS

| | | | |
|---|---|---|---|
| 2,566,208 A | 8/1951 | Jenkins | |
| 3,083,242 A | 3/1963 | Ramsden | |
| 3,226,450 A | 12/1965 | Blazejak et al. | |
| 3,558,671 A | 1/1971 | Martin | |
| 3,563,751 A | 2/1971 | Cohen | |
| 3,963,769 A * | 6/1976 | Fukunaga | 558/375 |
| 4,003,943 A * | 1/1977 | Fukunaga | 558/378 |
| 4,005,091 A * | 1/1977 | Fukunaga | 560/124 |
| 4,066,569 A | 1/1978 | Lim | |
| 4,133,821 A | 1/1979 | West et al. | |
| 4,618,453 A | 10/1986 | Kim | |
| 4,960,916 A | 10/1990 | Pazik et al. | |
| 5,093,698 A | 3/1992 | Egusa | |
| 5,110,835 A | 5/1992 | Walter et al. | |
| 5,247,226 A | 9/1993 | Sato et al. | |
| 5,281,730 A | 1/1994 | Zambounis et al. | |
| 5,292,881 A | 3/1994 | Berneth et al. | |
| 5,393,614 A | 2/1995 | Nakada | |
| 5,556,524 A | 9/1996 | Albers | |
| 5,811,833 A | 9/1998 | Thompson | |
| 5,840,217 A | 11/1998 | Lupo et al. | |
| 5,922,396 A | 7/1999 | Thompson et al. | |
| 6,013,384 A | 1/2000 | Kido et al. | |
| 6,013,982 A | 1/2000 | Thompson et al. | |
| 6,103,459 A | 8/2000 | Diel et al. | |
| 6,207,835 B1 | 3/2001 | Reiffenrath et al. | |
| 6,350,534 B1 | 2/2002 | Boerner et al. | |
| 6,423,429 B2 | 7/2002 | Kido et al. | |
| 6,524,728 B1 | 2/2003 | Kijima et al. | |
| 6,700,058 B2 | 3/2004 | Nelles et al. | |
| 6,747,287 B1 | 6/2004 | Toguchi et al. | |
| 6,824,890 B2 | 11/2004 | Bazan et al. | |
| 6,908,783 B1 | 6/2005 | Kuehl et al. | |
| 6,972,334 B1 | 12/2005 | Shibanuma et al. | |
| 7,081,550 B2 | 7/2006 | Hosokawa et al. | |
| 7,345,300 B2 | 3/2008 | Qin | |
| 2003/0064248 A1 | 4/2003 | Wolk | |
| 2003/0165715 A1 | 9/2003 | Yoon et al. | |
| 2003/0234397 A1 | 12/2003 | Schmid et al. | |
| 2004/0068115 A1 | 4/2004 | Lecloux et al. | |
| 2004/0076853 A1 | 4/2004 | Jarikov et al. | |
| 2005/0040390 A1 | 2/2005 | Pfeiffer et al. | |
| 2005/0061232 A1 | 3/2005 | Werner et al. | |
| 2005/0072971 A1 | 4/2005 | Marrocco et al. | |
| 2005/0086251 A1 | 4/2005 | Hatscher et al. | |
| 2005/0110009 A1 | 5/2005 | Blochwitz-Nimoth et al. | |
| 2005/0121667 A1 | 6/2005 | Kuehl et al. | |
| 2006/0049397 A1 | 3/2006 | Pfeiffer et al. | |
| 2007/0026257 A1 | 2/2007 | Begley et al. | |
| 2007/0058426 A1 | 3/2007 | Sokolik et al. | |
| 2007/0090371 A1 | 4/2007 | Drechsel et al. | |
| 2007/0116984 A1 | 5/2007 | Park et al. | |
| 2007/0145355 A1 | 6/2007 | Werner et al. | |
| 2007/0252140 A1 | 11/2007 | Limmert et al. | |
| 2008/0103315 A1 | 5/2008 | Egawa et al. | |
| 2008/0122345 A1 | 5/2008 | Sakata et al. | |
| 2008/0145708 A1 | 6/2008 | Heil et al. | |
| 2008/0265216 A1 * | 10/2008 | Hartmann et al. | 252/500 |
| 2009/0001327 A1 | 1/2009 | Werner et al. | |
| 2010/0026176 A1 * | 2/2010 | Blochwitz-Nomith et al. | 313/504 |
| 2010/0288362 A1 * | 11/2010 | Hatwar et al. | 136/263 |

FOREIGN PATENT DOCUMENTS

CA 2549309 9/2005
(Continued)

OTHER PUBLICATIONS

Hopf et al., "Preparation and Properties, Reactions, and Applications of Radialenes"; Angewandte Chemie, vol. 31, No. 8, Aug. 1992, pp. 921-1100.
G. Seitz, Nachr. Chem. Tech. Lab 28 (1980), No. 11, extract pp. 804-807, total pp. 6; "Pseudooxokohlenstoffe".
Pfeiffer et al., "Controlled Doping of Phthalocyanine Layers by Cosublimation with Acceptor Molecules: A Systematic Seebeck and Conductivity Study"; Applied Physics Letters, vol. 73, No. 22, Nov. 20, 1998, pp. 3202-3204.

(Continued)

*Primary Examiner* — Douglas Mc Ginty
(74) *Attorney, Agent, or Firm* — Sutherland, Asbill & Brennan, LLP

(57) ABSTRACT

The present invention relates to radialene compounds as well as to their use as doping agent for doping an organic semiconductive matrix material, as blocker material, as charge injection layer, as electrode material as well as organic semiconductor, as well as electronic components and organic semiconductive materials using them.

11 Claims, No Drawings

FOREIGN PATENT DOCUMENTS

| | | |
|---|---|---|
| CH | 354065 | 5/1961 |
| CH | 354066 | 5/1961 |
| DE | 19836408 | 2/2000 |
| DE | 10261662 | 7/2004 |
| EP | 1000998 | 5/2000 |
| JP | 61254582 | 11/1986 |
| JP | 63172274 | 7/1988 |
| JP | 63172275 | 7/1988 |
| JP | 04338760 | 11/1992 |
| JP | 7168377 | 7/1995 |
| JP | 2004002740 A * | 1/2004 |
| JP | 2004002741 A * | 1/2004 |
| JP | 2004010703 | 1/2004 |
| JP | 2004335557 | 11/2004 |
| WO | WO 03/088271 | 10/2003 |
| WO | WO 03/104237 | 12/2003 |
| WO | WO 2006/067800 | 6/2006 |
| WO | WO 2008/022633 | 2/2008 |

OTHER PUBLICATIONS

Schmidt, "Reaktionen von Quadratsaure and Quadratsaure-Derivaten", Synthesis, Dec. 1980, extract pp. 966-968, 24 total pages.
West et al., "Diquinocyclopropanones, Diquinoethylenes, and the Anion-Radical and Free-Radical Intermediates in their Formation", Dept. of Chemistry, University of Wisconsin, Feb. 24, 1975; pp. 2295-2299.
Takahashi et al., "Novel Electron Acceptors for Organic Conductors: 1,2-Bis . . . "; J. Chem. Soc., Chem. Commun., 1994, pp. 519-520.
T. Fukunaga et al., "Negatively Substituted Trimethylenecyclopropane Dianions"; JACS 1976, pp. 610-613.
Koster et al., "Synthesis and Reactions of a Tetraquinocyclobutane", Dept. of Chemistry, University of Wisconsin, J. Org. Chem., vol. 40, No. 16, 1975, pp. 2300-2304.
Sprenger et al., "The Cyclobutenediylium Cation, a Novel Chromophore from Squaric Acid", Angew. Chem. internat. Edit., vol. 6 (1967), No. 6, pp. 553-554.
Auch et al., "Eine neue Synthese and die Kristallstrukturanalyse von,, Krokonat-Blau . . . ", Chem. Ber. 120, 1691-1969 (1987), extract pp. 1691-1693, 6 total pages.
Blinka et al., "Octacyanotetramethylenecyclobutane Dianion and its Anion-Radical", Tetrahedron Lett. (1983), vol. 24 No. 1567-1569.
Fatiadi, Pseudooxocarbons, Synthesis of 1,2,3-Tris (dicyanomethylene) croconate Salts; A New Bond-Delocalized Dianion, Croconate Blue, J. Org. Chem. 1980, 45, 1338-1339.
Fatiadi, "Synthesis of 1,3-(Dicyanomethylene) croconate Salts. New Bond-Delocalized Dianion, Croconate Violet", Journal of the American Chemical Society, Apr. 12, 1978, pp. 2586-2587.
Fatiadi et al., "Electrochemical Oxidation of Several Oxocarbon Salts in N,N-Dimethylformamide", J. Electroanal Chem. (1982) 135 193-209.
Hopf et a., "Uber einen neuen Kohlenwasserstoff C18H24 . . . ", Helvetica Chimica Acta, vol. XLIV, issue II (1961), No. 46, extract from p. 384, 5 pages total.
Blochwitz et al., "Low Voltage Organic Light Emitting Diodes Featuring Doped Phthalocyanine as Hole Transport Material", Applied Physics Letters, vol. 73, No. 6, Aug. 10, 1998, pp. 729-731.
Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).
Akutagawa, T. et al. "Multi Electron and Proton-Transfer System Based on 2,2'-biimidazole derivatives," Science and Technology of Syn. Metals, 1994, 346.
Alonso, R. A. et al. "Photostimulated Reaction of Diphenylarsenide and Diphenylstibide Ions with Haloaromatic Compounds by the Srn1 Mechanism. Electron Transfer vs. Bond Breaking of the Radical Anion Intermediate," J. Org. Chem. (1982) 47(1) pp. 77-80.
Bach, U. et al. "Solid-state dye-sensitized mesoporous $TiO_2$ solar cells with high photon-to-electron conversion efficiencies," Nature, vol. 395, Oct. 8, 1998, pp. 583-585.
Bamgboye, T.T. et a. "Lewis acidity of Ph2SbX3, wherein X = Cl or Br. Crystal structures of Ph2SbC13*H20 and Ph2SbBr3*MeCN," J. of Organometallic Chem. vol. 362, Feb. 28, 1989, pp. 77-85.
Barton, D.H.R. et al. "Comparative Arylation Reactions with Pentaphenylbismuth and with Triphenylbismuth Carbonate," J. Chem. Soc. Chem. Commun. (1980) 17, pp. 827-829.
Baumgartel, H. et al., "Polarographische Untersuchungen zur Konformation von 1.2.3.4.5-pentaarylimidazoliumkationen," Ber. Bunsenges (1972) 76/2, 94-100.
Baumgartel, H. et al.,"Uber eine neue Synthese von tetraaryl-imidazolen and pentaaryl-imidazolium-salzen," Chem. Ber. (1968), 101, 3504.
Bhattacharya, S.N. et al. "Preparation & Characterization of Some Triarylarsenic & Triarylantimony Mixed Halides & Related Compounds," Indian J. Chem. 16A (1978) pp. 778-781.
Bonati, F. et al. "Reactions of C-imidazolyllithium derivatives with Broup Ib compounds: tris[micro-(1-alkylimidazolato-N3, C2)]tri-gold (I) and-silver (I)," J. Organomet. Chem. 1989, 375, pp. 147-160.
Brucsis, L. et al. "Substituionasreaktionen an 1,4-dihalogen-2,3,5,6-tetracyan-benzolen," Chem. Ber. 109(1976) pp. 2469-2474.
Cherkashin M. I. et al. "Studies on 2,4,5-triarylimidazoles," Izv. Akad. Nauk SSSR, Seriya Khim. 1982, 2, pp. 376-377.
Chonan et al. "The synthesis of difluoro and dimethyl derivatives of 2,6-bis(dicyanomethylene)-2,6-dihydro-4H-cyclopenta[2,1-b:3,4-b']-dithiophen-4-one (CPDT-TCNQ) and the Conducting Properties of the Metallic Salts Based on the Dimethy Derivative," The Chemical Society of Japan (2004) pp. 1487-1497.
Curini, M. et al., "Ytterbium Triflate Promoted Synthesis of Benzimidazole Derivatives," Synlett, No. 10, pp. 1832-1834, 2004.
Dedik, S.G. et al. "Tetrahalotetraazafulvalenes-new strong electron acceptors," Chemistry of Heterocyclic Compounds (A Translation of Khimiyageterotsiklicheskikh Soedinenii), Plenum Press Co., New York, U.S., vol. 10, Jan. 1, 1989, p. 1421.
Deluca, Mark et al., "The p-toluenesulfonic acid promoted synthesis of 2-substituted benzoxazoles and benzimidazoles from diacylated precursors," Tetrahedron, vol. 53, No. 2, pp. 457-464, 1997.
Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.
Fausett, B.W. et al. "Palladium-catalyzed coupling of thiol esters with aryl and primary and secondary alkyl organiindium reagents," J. Org. Chem. (2005) 70(12) pp. 4851-4853.
Fenghong Li et al., "Leuco Crystal Violet as a dopant for n-doping of organic thin films of fullerene C60," J. Phys. Chem. B 2004, 108, pp. 17076-17088.
Fild, Manfred et al. "Group VA pentafluorophenyl compounds. 14. Pentafluorophenyl-substituted phosphoranes," Zeitschrift Fuer Anorganische and Allgemeine Chemie, 439, pp. 145-152 (1978).
Gan, F. "Optical nonlinearity of hybrid and nanocomposite materials prepared by the Sol-Gel method," J. of Sol-Gel Science and Technology, 13, 559-563 (1998).
Ganzorig, C. et al., "p-Typed Semiconducts of Aromatic Diamines Doped with SbC15," Chemistry Letters 2000, pp. 1032-1033.
Gibbons, M.N. et al. "Multiply Bridged Diantimony Compounds," Phosphorus, Sulfur, & Silicon 93/94 (1994).
Giovanella, et al. "Electroluminescence from two fluorinated organic emitters embedded in polyvinyl carbazole," Applied Physics Letters, vol. 87, pp. 171910-1-3.
Glemser, O. et al. "Synthese von Tris-pentafluorphenylarsin,-stibin und-phosphin sowie von Trimethyl-pentafluor-phenylsilan," Angew. Chemie (1964) 76, 953.
Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.
Gregg, B.A. et al., "On the superlinear increase in conductivity with dopant concentration in excitonic semiconductors," Applied Physics Letters, vol. 84, No. 10, Mar. 8, 2004, pp. 1707-1709.
Grimmett, M. R., "Imidazole and benzimidazole synthesis," Tables of Contents, pp. 1-10, Academic Press, Harcourt Brace & Company, Publishers, London, San Diego, NY, Boston et al., 1997.

Gufeng, He et al., "High-efficiency and low-voltage p-i-n electrophosphorescent organic light-emitting diodes with double-emission layers," Applied Physics Letters, vol. 85, No. 17, Oct. 25, 2004, pp. 3911-3913.

Haddon, R.C. et al., "Conducting films of C60 and C70 by alkali-metal doping," Nature, vol. 350, Mar. 28, 1991, pp. 320-322.

Harris, G. S. et al. "The Reaction of Trispentafluorophenylstibine with Halogens and Interhalogens," J. Fluorine Chem. 37 (1987) pp. 247-252.

Heinze, J. et al., "Polarographic studies of the conformation of 1,2,3,4,5-pentaarylimidazolium cations," The Institute for Physical Chemistry at the University of Freiburg, pp. 1-22, 1972.

Hill, J. "Oxidative Dimerization of Benzimidazole," J. Org. Chem. 1963, 28, pp. 1931-1932.

Iyoda, et al. "Novel synthesis of hexaaryl[3]radialenes via dibromo[3]dendralenes," Tetrahedron Letters 41 (2000), 6 pgs.

Japp, F. et al. "Constitution of Glycosine," J. Chem. Soc. Trans. 1887, 51, pp. 552-557.

Jefferson, Alan M. and Suschitzky, H., "New Route to Nucleophillically Substituted o-phenylenediamines," J.C.S. Chem. Comm. pp. 189-190, 1997.

Jensen, W.B.; The Generalized Lewis Acid Based Concepts, John Wiley & Sons, New York, 1980, pp. 113-195.

Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.

Katz, H.E. et al., "Pyridyl Dicyanoquinodimethane Acceptors for Electroactive Solids," J. Org. Chem. 56 (1991) pp. 5318-5324.

Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179.

Kikuchi, A et al. "A new family of pi-conjugated delocalized biradicals: electronic structures of 1,4-bis(2,5-diphenylimidazol-4-ylidene)cyclohexa-2,5-diene," J. Phys. Chem. B., 2005, 109, pp. 19448-19453.

Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.

Kimura, M. et al. "Preparation of 4-(4,5-diphenyl-1H-imidazol-2-yl)benzaldehyde and Its Practical Synthetic Use in the Synthesis of Unsymmetrically Substituted Imidazoles," ITE Letters on Batteries, New Technologies and Medicine, 2002, 3, pp. 30-34.

Klopman, G. "Chemical Reactivity and the Concept of Charge-and Frontier-controlled reactions," Journal of the American Chemical Society., vol. 90, No. 2, Jan. 17, 1968, pp. 223-234.

Kozaki, M. et al. "Preparation, Properties, and Reduction of Heteroaromatic Quinoids with 1,4-diazacyclopentadien-2-ylidene Terminals," Org. Lett. 2005, 7, pp. 115-118.

Krebs, F.C. et al. "Superradiant properties of 4,4'-bis(1H-phenanthro[9,10-d]imidazol-2-yl)biphenyl and how a laser dye with exceptional stability can be obtained in only one synthetic step," Tetrahedron Lett. 2001, 42, pp. 6753-6757.

Kulkarni, A.P. et al., "Electron transport materials for organic light-emitting diodes," Chem. Mater. 2004, 16, pp. 4556-4573.

Lane, E.S. "A Modified Benziminazole Synthesis," J. Chem. Soc. 1953, pp. 2238-2240.

Lehmstaedt, K. et al. "Halogen-2,2'-diimidazole und ihre Umsetzungen mit Aminen zu Farbstoffen," Ber. Dt. Chem. Ges. B, 1943, pp. 879-891.

Leyden, R. et al. "Thermally Induced Degradation of 2,3,5,6-tetrachloroterephthalylidenebis(o-aminoaniline)," J. Org. Chem. 1983, 48, pp. 727-731.

Li, J. Y. et al. "Enhancement of green electroluminescence from 2,5-di-p-anisyl-isobenzofuran by double-layer doping strategy," Preparation and Characterization, vol. 446, No. 1, pp. 111-116.

Ludvik, J. and Pragst, F. et al., "Electrochemical generation of triplet states," Journal of Electroanalytical Chemistry, No. 180, pp. 141-156, (1984).

Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.

Maennig, B. et al., "Organic p-i-n solar cells," App. Phys. 2004, A 79, pp. 1-14.

Matschke, M. et al. "Bis-4h-imidazoles-tetraazafulvalenes-2,2'-biimidazoles: three variations of one redox system," Tetrahedron, vol. 62, No. 36, Sep. 4, 2006, pp. 8586-8590.

Mayer, U. et al. "Uber 2,3,6,7-tetraphenyl-1,4,5,8-tetraazafulvalen," Tetrahedron Lett. 1966, 42, pp. 5221-5223.

Mayer, U. et al. "Uber Biradikale, Chinone and Semichinone der Imidazolyl-Reihe," Angew. Chem. 1966, 78, p. 303.

Minoura, M. et al. "Hexaaryltellurium, the First Neutral Compounds Comprising Hexaarylated Elements," Angew. Chem. Int. Edit. 35 (22) pp. 2660-2662 (1996).

Miyasato, M. et al. "Syntheses and Reactions of Hexavalent Organitellurium Compounds Bearing Five or Six Tellurium-Carbon Bonds," Chem.-A European J. 10(10) pp. 2590-2600 (2004).

Muramatsu, T. et al, "Visible Light Sensitive Cyclomer and Its Tautomeric Dispiro Compound Formed from Bispyridiny Diradical," J. Am. Chem. Soc. 2005, 127, 4572-3.

Muramatsu, T. et al., "Photosensitive Cyclomer Formation of 1,1'-(1,2-ethanediyl)bis(pyridinyl) diradical and its derivativese," J. Am. Chem. Soc. 1989, 111, 5782-7.

Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).

Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.

Oeter, D. et al., "Doping and Stability of Ultrapure alpha-oligothiophene Thin Films," Synthetic Metals, 61, 1993, pp. 147-150.

Okada, K. et al. "Detection of a diradical intermediate in the cis-trans isomerization of 5,5'-bis(4,5-diphenyl-2H-imidazol-2-ylidene)-5,5'-dihydro-delta 2,2'-bithiophene," Tetrahedron Lett. 2006, 47, pp. 5375-5378.

Okada, K. et al. "Novel Dimers of 2,2'-(m-Phenylene)bis(4,5-diphenyl-1-imidazolyl) Diradical," Chem. Lett. 1998, pp. 891-892.

Otero, A. et a. "Pentachlorophenyl-arsenic,-antimony and-bismuth compounds," J. of Organometallic Chemistry, vol. 171, No. 3, Jan. 1, 1979, pp. 333-336.

Otero, A. et al. "Pentafluorophenylantimony compounds," J. Organometallic Chem. 154 (1978) pp. 13-19.

Ouchi, A. et al. "13C-nuclear magnetic resonance of some triaryl- and tri-alkylantimony and-bismuth derivatives," J. of Inorganic and Nuclear Chemistry, vol. 37, Issue 11, Nov. 1975, pp. 2347-2349.

Ouchi, A. et al. "The syntheses and properties of some alkylthioacetato and arylthioacetato derivatives of triphenylantimony(V) and-bismus (V)," J. of Inorganic and Nuclear Chemistry, vol. 37, Issue 12, Dec. 1975, pp. 2559-2561.

Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.

Parthasarathy, G. et al., "Lithium doping of semiconducting organic charge transport materials," J. Appl. Phys., vol. 89, No. 9, May 1, 2001, pp. 4986-4992.

Petzhold, C. "Beitrage zur Synthese funktioneller 1,4,5,8-tetraazafulvalene," Dissertation; Friedrich-Schiller-Universitat Jena; 2006.

Quast, H. and Schmitt, E.; "Note Regarding the Quaternization of Heterocycles," Institute of Organic Chemistry at the University of Wurzburg, Chem. Ber. 101, pp. 4012-4014, (1968).

Rake, A. T. et al. "Pentafluorophenyl and phenyl-phosphinidene ions and their group V analogues," Oms. Organic Mass Spectrometry, vol. 3 Jan. 1, 1970, pp. 237-238.

Rasmussen, P.G. et al. "Complexes of the New Ligand Tetracyanobiimidazole," J. Am. Chem. Soc. 1982, 104, pp. 6155-6156.

Rezende, M. C. et al. "An Alternative Preparation of Bisbenzimidazoles," Syn. Comm. 2001, 31, pp. 607-613.

Rezende, M. et al. "Puzzling Formation of Bisimidazole Derivatives from Hexachloroacetone and Diamines," Tetrahedron Lett. 1996, 37, 5265-5268.

Sakaino, Y. "Structures and Chromotropic Properties of 1,4-bis(4,5-diphenylimidazol-2-yl)benzene Derivatives," J. Org. Chem. 1979, 44, pp. 1241-1244.

Sato, S. et al. "Isolation and Molecular Structure of the Organopersulfuranes [12-S-6(C6)]," J. Am. Chem. Soc. 128(21) pp. 6778-6779 (2006).

Schneiders, P. et al. "Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.

Schwarz, W. M. et al., "Formation of Stable Free Radicals on Electroreduction of N-alkylpyridium salts," J. Am. Chem. Soc., 33 3164 (1961).

Sekine, T. et al. "Dimerizations of pi-Rich N-heteroaromatic compounds and xanthine derivatives," Chem. Pharm. Bull. 1989, 37, pp. 1987-1989.

Sharma, G.D. et al., "Influence of Iodine on the Electrical and Photoelectrical Properties of Zinc Phthalocyanine Think Film Devices," Materials Science and Engineering, B41, 1996, pp. 222-227.

Singhal, K. et al. "One the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.

Smith, M.B. Organic Synthesis, McGraw-Hill, Inc. 1994, Chapter 1.

Suschitzky, H. "Syntheses and Reactions of 2,2'-bisbenzimidazole Systems," J. Heterocyclic Chem. 1999, 36, pp. 1001-1012.

Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.

Takahashi et al. "Novel metallic charge-transfer complexes composed of a [3]radialene type acceptor: a 1,2-bis(p-benzoquino)-3-[2-(dicyanomethylene) . . . " Advanced Materials, July, No. 7, 3 pgs.

Vaid T.P. et al, "Investigations of the 9,10-diphenylacridyl radical as an isostructural dopant for the molecular semiconductor 9,10-diphenylanthracene," Chemistry of Materials, American Chemical Society, Bd. 15, Nr. 22, 4292-4299 (2003).

Vyas, P.C. et al. "A simple synthesis of 2,2'-bis-benzimidazoles," Chem. Industry, 1980, pp. 287-288.

Weiss, M. "Acetic Acid-Ammonium Acetate Reactions. 2-Isoimidazoles as Intermediates in Imidazole Formation," J. Am. Chem. Soc. 1952, 74, pp. 5193-5195.

Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).

Yamaguchi, et al., "New Approaches to Tetracyanoquinodimethane," Bull. Chem. Soc. Jpn. 62 (1989) pp. 3036-3037.

Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.

Yoshiko, S., et al. "The Quinoid-biradical Tautomerism of 3,6-bis(4,5-diphenyl-2H-imidazol-2-ylidene)-1,4-cyclohexadiene," Nippon Kagaku Kaishi, 1972, 1, pp. 100-103.

Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).

Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.

Ziegenbein, W. "The cyclobutenediylium cation, a novel chromophore from squaric acid," Angew. Chem., 79:12, pp. 581-582 (1967).

English Translation of Japanese Office Action; Japanese Patent Application No. 2005-228491; Apr. 17, 2009.

International Search Report, International App. No. PCT/EP2007/002359, May 24, 2007.

Final Office Action, U.S. Appl. No. 11/688,777; Nov. 27, 2009

Non-Final Office Action, U.S. Appl. No. 11/688,777; Feb. 2, 2009.

Response to Office Action, U.S. Appl. No. 11/688,777; Sep. 4, 2009.

Response to Office Action, U.S. Appl. No. 11/688,777; Aug. 3, 2009.

Restriction Requirement, U.S. Appl. No. 11/688,777; Mar. 5, 2010.

Response to Restriction Requirement, U.S. Appl. No. 11/688,777; Apr. 1, 2010.

Notice of Allowance, U.S. Appl. No. 11/196,491; Apr. 13, 2009.

Notice of Allowance, U.S. Appl. No. 11/196,491; Oct. 20, 2008.

Response to Office Action for U.S. Appl. No. 11/196,491; Aug. 11, 2008.

Final Office Action, U.S. Appl. No. 11/196,491; Feb. 11, 2008.

Response to Office Action for U.S. Appl. No. 11/196,491; Nov. 5, 2008.

Non-Final Office Action, U.S. Appl. No. 11/196,491; Jul. 3, 2007.

International Search Report and Preliminary Report on Patentability for PCT/DE2008/001080; Jul. 11, 2008.

International Search Report for PCT/DE2008/00654; Jun. 15, 2009.

International Search Report and Preliminary Report on Patentability for PCT/EP2006/010816; Feb. 9, 2007.

Advisory Action for U.S. Appl. No. 11/315,072 mailed Mar. 8, 2010.

Response to Final Office Action for U.S. Appl. No. 11/315,072; Feb. 17, 2010.

Final Rejection for U.S. Appl. No. 11/315,072; Nov. 16, 2009.

Response to Office Action for U.S. Appl. No. 11/315,072; Jul. 29, 2009.

Non-Final Rejection for U.S. Appl. No. 11/315,072; Apr. 29, 2009.

Non-Final Rejection for U.S. Appl. No. 11/315,072; Nov. 12, 2008.

Response to Office Action for U.S. Appl. No. 11/315,072; Feb. 10, 2009.

European Search Report for EP 07009366; Oct. 19, 2007.

International Search Report for PCT/EP2008/003792; Sep. 2, 2008.

Disclosure Pursuant to 37 C.F.R. 1.56 for U.S. Appl. No. 12/264,511 (submitted herewith).

Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.

Gao, W. et al., "Effect of electrical doping on molecular level alignment at organic-organic heterojunctions," Applied Physics Letters, vol. 82, No. 26, Jun. 30, 2003, pp. 4815-4817.

Harada, K. et al. "Organic Homojunction Diodes with a High Built-in Potential: Interpretation of the Current-Voltage Characteristics by a Generalized Einstein Relation," Phys. Rev. Lett. 94, 036601 (2005).

Huang, Jingsong et al., "Low-voltage organic electroluminescent devices using pin structures," Applied Physics Letters, vol. 80, No. 1, Jan. 7, 2002, pp. 139-141.

Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.

Miller, L.L. et al., "A simple comprehensive correlation of organic oxidation and ionization potentials," J. Org. Chem., 1972, vol. 37, No. 6, pp. 916-918.

Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.

Parker, "On the Problem of Assigning Values to Energy Changes of Electrode Reactions," Journal of the American Chemical Society, 96:17, Aug. 21, 1974, pp. 5656-5661.

R. Schlaf et al., "Homo/Lumo Alignment at PTCDA/ZnPc and PTCDA/ClInPc Heterointerfaces Determined by Combined UPS and XPS Measurements," J. Phys. Chem. B 1999, 103, pp. 2984-2992.

Tang, T.B. et al., "Ionization thresholds of merocyanine dyes in the solid state," Journal of Applied Physics, vol. 59, (1), Jan. 1986, pp. 5-10.

Werner, A. G. et al., "Pyronin B as a donor for n-type doping of organic thin films," Applied Physics Letters, vol. 82, No. 25, Jun. 23, 2003, pp. 4495-4497.

Yao, Fu et al., "Quantum-chemical predictions of Absolute standard redox potentials of diverse organic molecules and free radicals in acetonitrile," J. Am. Chem. Soc. 2005, 127, pp. 7227-7234.

Zhou, X. et al., "Very low operating voltage organic light-emitting diodes using a p-doped amorphous hole injection layer," Applied Physics Letters, vol. 78, No. 4, Jan. 22, 2001, pp. 410-412.

Zimmerman, T. et al. "Benzocycloalkenone und dihydro-2H, 7H-1-benzopyranone aus 2,4,6-triaryl-pyryliumsalzen und cycloalkan-1,2-dionen," J. Prakt. Chem. 331 pp. 306-318 (1989).

Non-Final Rejection for U.S. Appl. No. 12/046,620; Nov. 25, 2009.

Response to Restriction Requirement for U.S. Appl. No. 12/046,620; Aug. 24, 2009.

Restriction Requirement for U.S. Appl. No. 12/046,620; Jul. 22, 2009.

Bard, A. J., Faulkner, R.J., Electrochemical Methods: Fundamentals and Applications, Wiley, 2nd Ed., 2000 (Chapter 2).

D'Andrade, B.W. et al., "Relationship between the ionization and oxidation potentials of molecular organic semiconductors," Organic Electronics 6, 2005, pp. 11-20.

Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.

Kido, Junji et al., "Bright Organic Electroluminescent Devices Having a Metal-doped Electron-injecting Layer," Applied Physics Letters, vol. 73, No. 20, Nov. 16, 1998, pp. 2866-2868.

Pfeiffer, M, et al., "Doped Organic semiconductors: physics and application in light emitting diodes," Organic Electronics, Elsevier, Amsterdam, NL, vol. 4, No. 2/3, Sep. 2003, pp. 89-103, XP001177135, ISSN: 1556-1199.

Tang, C.W. et al., "Organic electroluminescent diodes," Applied Physics Letters, vol. 51, No. 12, Sep. 21, 1987, pp. 913-915.

\* cited by examiner

RADIALENE COMPOUNDS AND THEIR USE

CROSS-REFERENCE TO RELATED APPLICATIONS

This application claims priority to U.S. Provisional Patent Application No. 61/107,826, filed Oct. 23, 2008, and is a continuation-in-part of U.S. patent application Ser. No. 12/111,326, filed Apr. 29, 2008, now U.S. Pat. No. 7,981,324. The disclosure of U.S. Provisional Patent Application No. 61/107,826 is incorporated herein by reference.

The present invention relates to radialene compounds as well as to their use as organic doping agent for doping an organic semiconductive matrix material for changing its electrical properties, as blocker material as well as charge injection layer and as electrode material. The invention also relates to organic semiconductive materials as well as to electronic components in which the radialene compounds are used.

In the present application alicyclics in which all ring atoms are sp2-hybridized and to the extent possible carry exocyclic C—C double bonds are designated as radialenes, see also H. Hopf and G. Maas, Angew. Chem. (1992), 8, 955. The structure of radialenes is based on oxocarbon and pseudooxocarbon compounds. Oxocarbon- and pseudooxocarbon compounds are sufficiently known as non-benzoid aromatics, see, e.g., G. Seitz, Nachr. Chem. Tech. Lab. 28 (1980), pages 804-807. The first oxocarbon compound, potassium croconate, was produced by L. Gmelin in 1825 from potash and coal. Those compounds, in which at least one oxygen atom is replaced by another heteroatom, are designated as pseudooxocarbons, as is readily known to an expert in the art.

It has been known for several years that organic semiconductors can be heavily influenced regarding their electrical conductivity by doping. Such organic semiconductive matrix materials can be built up either from compounds with good electron donor properties or from compounds with good electron acceptor properties. Strong electron acceptors such as tetracyanoquinonedimethane (TCNQ) or 2,3,5,6-tetrafluoro-tetracyano-1,4-benzoquinonedimethane (F4TCNQ) have become known for the doping of electron donor materials (HT), M. Pfeiffer, A. Beyer, T. Fritz, K. Leo, Appl. Phys. Lett., 73 (22), 3202-3204 (1998). and J. Blochwitz, M. Pfeiffer, T. Fritz, K. Leo, Appl. Phys. Lett., 73 (6), 729-731 (1998). The acceptor molecules generate so-called holes by electron transfer processes in electron donor-like base materials (hole transport materials) and the conductivity of the base material is more or less significantly changed depend on the number and mobility of the holes. For example, N,N'-perarylated benzidines such as TPD or N,N',N"-perarylated starburst compounds such as the substance TDATA, or, however, also certain metal phthalocyanines, such as in particular zinc phthalocyanine ZnPc are known as matrix material with hole transport properties.

However, the previously described compounds have disadvantages for a technical use in the production of doped semiconductive organic layers or of corresponding electronic components with such doped layers since the manufacturing processes in large-scale production plants or those on a technical scale can not always be sufficiently precise, which results in high control- and regulating expense within the processes for achieving a desired product quality or in undesired tolerances of the products. Furthermore, there are disadvantages in the use of previously known organic acceptors with regard to electronic components such as light-emitting diodes (OLEDs), field effect transistors (FET) or solar cells themselves since the cited production difficulties in the handling of the doping agents can lead to undesired irregularities in the electronic components or in undesired ageing effects of the electronic components. However, it should be considered at the same time that the doping agents to be used have extremely high electron affinities (reduction potentials) and other properties suitable for the application case since, e.g., the doping agents also co-determine the conductivity or other electrical properties of the organic semiconductive layer under given conditions. The energetic positions of the HOMO (highest occupied molecular orbital) of the matrix material and of the LUMO (lowest unoccupied molecular orbital) of the doping agent are decisive for the doping effect.

The present invention has the task of overcoming the disadvantages of the state of the art, in particular to make new organic mesomeric compounds available that can be used in particular as doping agent for the doping of organic semiconductors, that can furthermore be more readily handled in the production process and that result in electronic components whose organic semiconductive materials can be reproducibly manufactured. Especially, hole transport materials with a deep HOMO shall be dopable by the new organic mesomeric compounds.

This task is solved by the independent claims of the present application. Preferred embodiments are disclosed in the subclaims.

In the compounds in accordance with the invention the position of the LUMO is so low that further technically interesting hole transport materials can now be efficiently doped for the first time. Due to the extremely low position of the LUMO and to the associated high reduction potential of the compounds even performance efficiencies of solar cells can be significantly improved. The doping effect of a certain magnitude (e.g. a doped layer of a certain conductivity) can be achieved with a substantially lower amount of dopant material to be used compared to conventional dopant under otherwise unchanged conditions. In addition, these compounds are extremely diffusion-stable in organic layers on account of their high polarity. By making available radialenes as doping agents, these make possible a sufficient electrical conductivity of the organic semiconductive matrix given advantageous electron affinity of the doping agents in the particular components at low diffusion coefficients that ensure a component structure that is stable in time. Furthermore, the charge carrier injection of contacts into the doped layer can be improved by the doping agents. Furthermore, the doped organic semiconductive material and the resulting electronic component can have an improved long-time stability on account of the compounds used in accordance with the invention. This concerns, e.g., a reduction or loss of the conductivity over time. This furthermore concerns the stability of the doped layer that is arranged adjacent to non-doped layers of an electro-optical component so that electro-optical components with increased long-time stability of the electro-optical properties such as light emission quantum yield or, effectiveness of a solar cell or the like result.

[3]-radialene compounds[3]-radialene compounds as disclosed in the claims as disclosed in the claims have been found to be specifically useful to perform the invention. Those compounds are able to dope all common OLED hole transport materials. Especially, hole transport materials with a deep HOMO can be doped.

[3]-radialene compounds as disclosed in the claims are strong electron acceptors and form easily radical ion salts (where the [3]-radialene compound can carry for instance one, two or more negative charges) or charge-transfer complexes with electron donor compounds. Such radical ion salts or charge-transfer complexes have a variety of different useful applications such as to for charge injection layers, charge transport layers, organic conductor bodies, ferromagnetic bodies, or electrochromic or photochromic bodies.

By performing doping experiments, it was found that the compounds used in the examples below give good doping properties. It is especially important to note that the substitution pattern defined by those compounds give strongly accepting compounds with a reduction potential in the range of 0V vs. Fc/Fc+ to 0.4V vs. Fc/Fc+. Fc/Fc+ denoted as usual the Ferrocene/Ferrocenium redox couple. Reduction potentials can be considered as measures for the LUMO of a molecule. Favorable substitution patterns involve six-membered (hetero-) cycles fully substituted with acceptor units such as cyano, fluoro, chloro, bromo and the like, as functional unit in the cyclopropane compound. The six-membered (hetero-) cycles can be for instance perfluoropyridin-4-yl, tetrafluoro-4-(trifluoromethyl)phenyl), 4-cyanoperfluorophenyl, dichloro-3,5-difluoro-4-(trifluoromethyl)phenyl, and perfluorophenyl.

For p-doped OLED or organic solar cell, often hole-injecting materials such as phthalocyanine copper complex (CuPc), 4,4',4"-tris(N-3-methylphenyl-N-phenyl-amino)triphenylamine (m-MTDATA), 4,4',4"-tris(N-(2-naphthyl)-N-phenyl-amino)triphenylamine (2-TNATA) or MeO-TPD (N,N,N',N'-tetrakis(4-methoxy-phenyl)benzidine), or Spiro-TTB (2,2',7,7'-Tetrakis-(N,N-diphenylamino)-9,9'-spirobifluoren, also called Spiro-TTP) are doped by acceptor materials. The layer sequence is then for instance: Anode/p-doped HIL/EBL/EML/ETL/LiF/Cathode. Herein, HIL denotes a hole injection layer, EBL denotes a electron blocking layer, EML denotes a (light) emitting layer, ETL denoted an electron transport layer, LiF denotes Lithium fluoride layer. Such HIL materials have typically a relatively low oxidation potential in the range of 0V to 0.1V vs. Fc/Fc+. Oxidation potential can be considered as a measure for the HOMO of a molecule. There is a need, however, to achieve good doping results also in host materials which are conventionally used as HTL or EBL materials. They often have a higher oxidation potential in the range of 0.2 to 0.4 V vs. Fc/Fc+. It is remarkable, that the selected dopants provide the same high conductivities in a HIL type host and a HTL type host. HTL type materials are for instance: N,N'-Bis(naphthalen-1-yl)-N,N'-bis(phenyl)-benzidine, N,N'-Bis(naphthalen-1-yl)-N,N'-bis(phenyl)-9,9-spiro-bifluorene, 9,9-Bis[4-(N,N-bis-biphenyl-4-yl-amino)phenyl]-9H-fluorene, N,N'-bis(phenanthren-9-yl)-N,N'-bis(phenyl)-benzidine, 2,2'-Bis[N,N-bis(biphenyl-4-yl)amino]9,9-spiro-bifluorene, 1,3,5-tris {4-[bis(9,9-dimethyl-fluoren-2-yl)amino]phenyl}benzene, tri(terphenyl-4-yl)amine.

The deposition rate on a substrate with the compound used in accordance with the invention can be determined, e.g., using a quartz thickness monitor, as is customarily used, e.g., in the production of OLEDs. In particular, the ratio of the deposition rates of matrix materials and doping agent can be measured by independent measurements of them using two separate quartz thickness monitors in order to adjust the doping ratio.

It is understood that the compounds used in accordance with the invention are preferably such that they evaporate more or less or practically non-decomposed. However, if necessary, even purposeful precursors can be used as doping source that release the compounds used in accordance with the invention, e.g., acid addition salts, e.g., of a volatile or non-volatile inorganic or organic acid, or their charge transfer complexes, which acids and/or electron donors are preferably not volatile or only slightly volatile or the charge transfer complex itself acts as doping agent.

The doping agent is preferably selected in such a manner that it generates a conductivity just as high as or preferably higher than F4TCNQ under conditions that are otherwise the same such as, in particular, doping concentration (molar ratio, doping agent:matrix, layer thickness, current strength) at a given matrix material (e.g., zinc phthalocyanine or another matrix material cited further below), e.g., a conductivity (s/cm) greater than/equal to 1.1 times, 1.2 times or greater than/equal to 1.5 times or twice that of F4TCNQ as doping agent.

The doping agent used in accordance with the invention is preferably selected in such a manner that the semiconductive organic material doped with it still has ≧20%, preferably ≧30%, especially preferably ≧50% or 60% of the conductivity (s/cm) of the value at 100° C. after a temperature change of 100° C. to RT (20° C.).

Preparation of Oxocarbon-, Pseudooxocarbon- and Radialene Structures

The first oxocarbon compound, potassium croconate, was produced by L. Gmelin in 1825 from potash and coal. Oxocarbons and their esters and halogenides preferably react with electron-rich compounds such as aliphatic and aromatic amines, aromatics and heteroaromatics. A. H. Schmidt, Synthesis (1980) 961. The reaction products from tetrachlorocyclopropene and phenols in the presence of Lewis acids or CH-acidic compounds by strong bases, such as, e.g., arylacetonitriles, 1,3-diketones, cyclopentadienes, malonodinitriles, acceptor-substituted diarylmethanes, electron-poor diheteroarylmethanes are especially suitable for applications in accordance with the invention. [3]-Radialenes are obtained after oxidation has taken place, R. West et al. J. Org. Chem. (1975) 40 2295; T. Kazuka, T. Shinji J. Chem. Soc. Chem. Commun. (1994) 519; T. Fukunaga et al. JACS (1976) 98 610.

Matrix Materials

The present invention describes suitable doping agents for organic semiconductive materials such as hole transport materials HT that are customarily used in OLEDs or organic solar cells. The semiconductive materials are preferably intrinsically hole-conducting. The following gives an exemplary description of materials that can be applied in conjunction with doping agents of the radialene type in accordance with the invention.

The matrix material can consist partially (>10 or >25% by weight) or substantially (>50% by weight or >75% by weight) or totally of a metal phthalocyanine complex, a porphyrine complex, especially metal porphyrine complex, oligothiophene-, oligophenyl-, oligophenylene vinylene- or oligofluorene compound, in which the oligomer preferably comprises 2-500 or more, preferably 2-100 or 2-50 or 2-10 or more monomeric units. The oligomer can also comprise >4, >6 or >10 or more monomeric units, in particular also for the above-indicated ranges, thus, e.g., 4 or 6-10 monomeric units, 6 or 10-100 monomeric units or 10-500 monomeric units. Polymeric matrix materials can also be used. The monomers and oligomers can be substituted or unsubstituted and even block- or mixed polymerizates of the cited oligomers can be present as well as a compound with a triarylamine unit or a spiro-bifluorene compound. The cited matrix materials can also be present in combination with each other, optionally also in combination with other matrix materials. The matrix materials can have electron-donating substitutents such as alkyl- or alkoxy groups that have a reduced ionizing energy or reduce the ionizing energy of the matrix material.

The metal phthalocyanine complexes or porphyrine complexes used as matrix material can have a main group metal atom or subgroup metal atom. The metal atom Me can be coordinated 4-, 5- or 6-fold, e.g., in the form of oxo- (Me=O), dioxo- (O=Me=O) imine-, diimine-, hydroxo-, dihydroxo-, amino- or diamino complexes, without being limited to them. The phthalocyanine complex or porphyrine complex can each be partially hydrogenated, however, the mesomeric ring system is preferably not disturbed. The phthalocyanine can contain, e.g., magnesium, zinc, iron, nickel, cobalt, magnesium, copper or vanadyl (=VO) as central atom. The same or other metal atoms or oxometal atoms can be present in the case of porphyrine complexes.

In particular, such dopable hole transport materials HT can be arylated benzidines, e.g., N,N'-perarylated benzidines or other diamines such as of the type TPD (in which one, several or all of the aryl groups can have aromatic heteroatoms), suitable arylated starburst compounds such as N,N',N''-perarylated starburst compounds such as the compound TDATA (in which one, several or all of the aryl groups can have aromatic heteroatoms). The aryl groups can comprise phenyl, naphthyl, pyridine, quinoline, isoquinoline, peridazine, pyrimidine, pyrazine, pyrazole, imidazole, oxazole, furan, pyrrole, indole or the like, especially for each of the above-cited compounds. The phenyl groups of the particular compounds can be partially or completely replaced by thiophene groups.

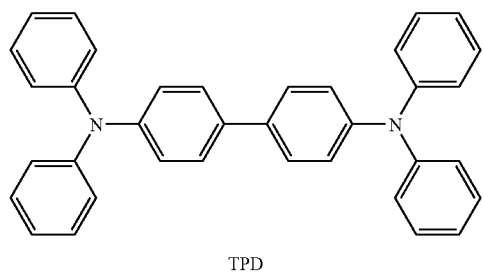

TPD

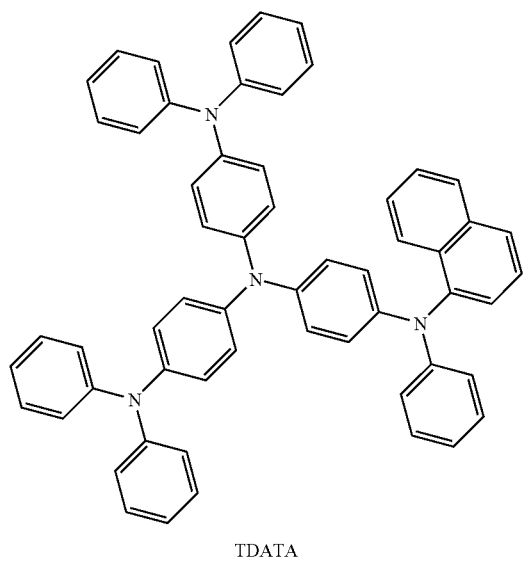

TDATA

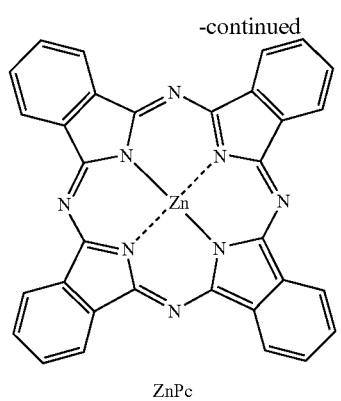

ZnPc

It is understood that even other suitable organic matrix materials, in particular hole-conducting materials can be used that have semiconductive properties.

Doping

The doping can take place in particular in such a manner that the molar ratio of matrix molecule to doping agent, or in the case of oligomeric matrix materials the ratio of matrix monomer number to doping agent is 1:100000, preferably 1:10000, especially preferably 1:5 to 1:1000, e.g., 1:10 to 1:100, e.g., ca. 1:50 to 1:100 or also 1:25 to 1:50.

Evaporation of the Doping Agents

The doping of the particular matrix material (preferably indicated here as hole-conducting matrix material HT) with the doping agents to be used in accordance with the invention can be produced by one or a combination of the following processes:

a) Mixed evaporation in the vacuum with a source for HT and one for the doping agent.
b) Sequential deposition of HT and doping agent with subsequent inward diffusion of the doping agent by thermal treatment
c) Doping of an HT layer by a solution of doping agent with subsequent evaporation of the solvent by thermal treatment
d) Surface doping of an HT layer by a layer of doping agent applied on either or both surfaces of the HT layer.
e) Making a solution of host and dopant and form a film from the solution for instance by coating, casting or printing techniques or other film making techniques known to a person skilled in the art.

The doping can take place in such a manner that the doping agent is evaporated out of a precursor compound that releases the doping agent under heating and/or irradiation. The irradiation can take place by electromagnetic radiation, especially visible light, UV light or IR light, e.g., by laser light or also by other radiation types. The heat necessary for evaporation can substantially be made available by the irradiation and can also be radiated in a purposeful manner into certain bands of the compounds or precursors or compound complexes such as charge transfer complexes to be evaporated in order to facilitate the evaporation of the compounds by dissociation of the complexes by conversion into excited states.

It is understood that the evaporation conditions described in the following are directed to those without irradiation and that uniform evaporation conditions are to be used for purposes of comparison.

For example, the following can be used as precursor compounds:

a) Mixtures or stoichiometric or mixed crystalline compounds of the doping agent and an inert, non-volatile substance, e.g., a polymer, molecular sieve, aluminum oxide, silica gel, and oligomers or another organic or inorganic substance with high evaporation temperature, in which the doping agent is bound primarily by van der Waals forces and/or hydrogen bridge bonding to this substance.

b) Mixture or stoichiometric or mixed crystalline compound of the doping agent and one non-volatile compound V more or less of the electron donor type, in which a more or less complete charge transfer occurs between the doping agent and the compound V as in charge transfer complexes with more or less electron-rich polyaromatics or heteroaromatics or another organic or inorganic substance with high evaporation temperature.

c) Mixture or stoichiometric or mixed crystalline compound of the doping agent and a substance that evaporates together with the doping agent and has the same or higher ionizing energy as the substance HT to be doped, so that the substance does not form a trap for holes in the organic matrix material. According to the invention the substance can also be identical to the matrix material here, e.g., be a metal phthalocyanine or benzidine derivative. Further suitable volatile co-substances such as hydroquinones, 1,4-phenylene diamines or 1-amino-4-hydroxybenzene or other compounds form quinhydrones or other charge transfer complexes.

Electronic Component

A plurality of electronic components or equipment containing them can be produced using the organic compounds in accordance with the invention for producing doped organic semiconductive materials that can be arranged in particular in the form of layers or electrical line paths. In particular, the doping agents in accordance with the invention can be used to produce organic, light-emitting diodes (OLED), organic solar cells, organic diodes, especially those with a high rectification ratio such as $10^3$-$10^7$, preferably $10^4$-$10^7$ or $10^5$-$10^7$ or organic field effect transistors. The conductivity of the doped layers and/or the improvement of the charge carrier injection of contacts into the doped layer can be improved by the doping agents in accordance with the invention. In particular in the case of OLEDs or solar cells the component can have a pin structure (the device has a one or more p-doped hole transport layers and/or one or more n-doped electron transport layers) or an inverted structure (the top-electrode and hole transport layer are located on the same side from the light emitting or light harvesting layer while the substrate is on the opposite side) without being limited to them. An injection layer can be made, for instance, by forming a layer containing or consisting of the organic compounds in accordance with the invention between an electrode and a charge transporting layer. However, the use of the doping agents in accordance with the invention is not limited to the advantageous exemplary embodiments cited above.

Exemplary Embodiments

The invention will be explained in detail with a few exemplary embodiments. The compounds in accordance with the invention will now be used in the following manner as doping agents for different hole conductors that for their part are used for constructing certain microelectronic or optoelectronic components such as, e.g., an OLED. The doping agents can be co-evaporated with the hole transport materials of the matrix in high vacuum (ca. $2\times10^{-4}$ Pa) by thermal evaporation. A typical deposition rate for the matrix material is 0.2 nm/s (density ca. 1.5 g/cm$^3$). The evaporation rates for the doping agents can vary between 0.001 and 0.5 nm/s (assuming the same density) in accordance with the desired doping ratio.

In the following examples the current measurements were carried out over a current path of the doped HT material 1 mm long and ca. 0.5 mm wide at 1V. under these conditions ZnPc conducts practically no electrical current.

SYNTHESIS OF EXAMPLES

1. Ethyl 2-cyano-2-aryl Acetates a), b), c), d) and e)

General Procedure:

To a solution of 207 mmol of the either starting material A, B, C, D or E and 250 mmol of potassium carbonate in 370 ml of dimethylformamide 207 mmol of cyano acetic ester in 50 ml of dimethylformamid were added quickly. The mixture was allowed to stir for 48 h at room temperature. Then the reaction suspension was poured into a 3 l beaker with 1 l of ice water. While stirring the solution was acidified with 100 mL of conc. acetic acid. The aqueous solution was extracted four times with chloroform in this order (250 mL, 150 mL, 100 mL, 100 mL). After drying the combined organic layers with magnesium sulphate the solvent was removed in vacuum. The remaining oil was used in the next step without any further purification.

a) Ethyl 2-cyano-2-(perfluorophenyl)acetate

Hexafluorobenzene (A) has been used as starting material. 51.9 g of the ester were obtained according to the procedure described above.

b) Ethyl 2-cyano-2-(perfluoropyridin-4-yl)acetate

Pentafluoropyridin (B) has been used as starting material. 47.7 g of the ester were obtained according to the procedure described above.

c) Ethyl 2-cyano-2-(4-cyanoperfluorophenyl)acetate

Pentafluorobenzonitril (C) has been used as starting material. 54.3 g of the ester were obtained according to the procedure described above.

d) Ethyl 2-cyano-2-(4-trifluoromethylperfluorophenyl)acetate

Octafluorotoluol (D) has been used as starting material. 66.8 g of the ester were obtained according to the procedure described above.

e) Ethyl 2-cyano-2-(4-trifluoromethyl-2,6-dichloro-3,5-difluorophenyl)acetate 4-trifluoromethyl-2,6-dichloro-1,3,5-trifluorobenzene (E) has been used as starting material. 64.8 g of the ester were obtained according to the procedure described above.

2. Aryl Acetonitriles f), g), h), i) and k)

General Procedure:

In a 250 mL round bottom flask the whole amount of the ethyl 2-cyano-2-aryl acetate a), b), c) d) or e) as synthesized above was dissolved in 84 ml of acetic acid (50%) together with 4.15 ml of sulfuric acid (conc.). The mixture was heated on reflux for 16 hours. After cooling to room temperature the mixture was poured into a 500 mL beaker with 120 mL of ice water and stirred over a period of 30 min. The organic layer was separated and the aqueous layer extracted with 100 mL of chloroform. The combined organic layers were washed with 100 mL of water and with 100 mL of saturated sodium bicarbonate solution. After drying the organic layer with magnesium sulphate the solvent was removed in vacuum to give brown coloured oil. Distillation in vacuum gave a colourless slow solidifying liquid.

f) Pentafluorophenyl Acetonitrile

Ethy-2-cyano-2-(perfluorophenyl)acetate (a) was used as starting material. 36.4 g (176 mmol; 85% based on starting material A) of the aryl acetontrile were obtained according to the procedure described above.

g) 4-(cyanomethyl)-2,3,5,6-tetrafluoropyridine

Ethyl 2-cyano-2-(perfluoropyridin-4-yl)acetate (b) was used as starting material. 33.1 g (174 mmol; 84% based on starting material B) of the aryl acetontrile were obtained according to the procedure described above.

h) 4-(cyanomethyl)-2,3,5,6-tetrafluorobenzonitril

Ethyl-2-cyano-2-(4-cyanoperfluorophenyl)acetate (c) was used as starting material. 39.0 g (182 mmol; 88% based on starting material C) of the aryl acetontrile were obtained according to the procedure described above.

i) 2-(2,3,5,6-tetrafluoro-4-(trifluoromethyl)phenyl) acetonitrile

Ethyl-2-cyano-2-(4-trifluoromethylperfluorophenyl)acetate (d) was used as starting material. 48.8 g (190 mmol; 92% based on starting material D) of the aryl acetontrile were obtained according to the procedure described above.

k) (4-trifluoromethyl-2,6-dichloro-3,5-difluorophenyl)acetonitrile

Ethyl-2-cyano-2-(4-trifluoromethyl-2,6-dichloro-3,5-difluorophenyl)acetate (e) was used as starting material. 53.4 g (184 mmol; 89% based on starting material E) of the aryl acetontrile were obtained according to the procedure described above.

3. [3]-radialenes l), m), n), o) and p)

General Procedure:

Lithium hydride (98%) is suspended in 600 mL of 1,2-dimethoxyethane and cooled to 0° C. 152 mmol of aryl acetonitrile f), g), h), i) or k) was dissolved in 60 mL of 1,2-dimethoxyethane and added over a period of 10 to 15 min. The ice bath has been removed and the reaction was allowed to warm up over 45 min. After 15 min stirring at room temperature the mixture was cooled to 0° C. again. 7.12 g (40.0 mmol) of perchlorocycloprop-1-ene in 40 mL of 1,2-dimethoxyethane were added dropwise. The colour of the solution turned to dark red. The dark solution was kept on stirring for 44 h while warming up to room temperature. Then the reaction suspension was poured into a 2 L beaker with 1.2 L of ice water. The stirring solution was acidified with concentrated hydrochloric acid to pH=1 (240 mL HCl) and extracted with ethyl acetate (3×500 mL). The combined organic layers were washed in the following order with brine, water and bicarbonate solution and then with water again. The combined organic layers were dried with magnesium sulphate and the solvent was carefully removed in vacuum to give a dark coloured material which was directly used in the next transformation without any further purification.

The dark coloured material was dissolved in 1400 mL of acetic acid (100%) and treated with a mixture of 360 mL hydrobromic acid (48%) and 120 mL of nitric acid (65%) prepared approximately ten minutes before. The resulting mixture was stirred for 1.5 hours. The mixture was filtrated and the resulting orange precipitate was washed with water and dried in vacuum to afford the crude material. The crude material was purified by gradient sublimation.

l) (2E,2'E,2"E)-2,2',2"-(cyclopropane-1,2,3-triylidene)tris(2-(perfluorophenyl)-acetonitrile)

Pentafluorophenyl acetonitrile (f) was used as starting material. 9.37 g (14.4 mmol; 36% based on tetrachlorocyclopropene) of the [3]radialene were obtained after gradient sublimation according to the procedure described above.
Mp. 211° C.

m) (2E,2'E,2"E)-2,2',2"-(cyclopropane-1,2,3-triylidene)tris(2-(perfluoropyridin-4-yl)-acetonitrile)

4-(cyanomethyl)-2,3,5,6-tetrafluoropyridine (g) was used as starting material. 8.40 g (14.0 mmol; 35% based on tetra-chlorocyclopropene) of the [3]radialene were obtained after gradient sublimation according to the procedure described above.
Mp. 140° C.

n) (2E,2'E,2"E)-2,2',2"-(cyclopropane-1,2,3-triylidene)tris(2-(4-cyanoperfluorophenyl)-acetonitrile)

4-(cyanomethyl)-2,3,5,6-tetrafluorobenzonitrile (h) was used as starting material. 10.2 g (15.2 mmol; 38% based on tetrachlorocyclopropene) of the [3]radialene were obtained after gradient sublimation according to the procedure described above.
Mp. 316° C.

o) (2E,2'E,2"E)-2,2',2"-(cyclopropane-1,2,3-triylidene)tris(2-(2,3,5,6-tetrafluoro-4-(trifluoromethyl)phenyl)-acetonitrile)

2-(2,3,5,6-tetrafluoro-4-(trifluoromethyl)phenyl)acetonitrile (i) was used as starting material. 12.8 g (16.0 mmol; 40% based on tetrachlorocyclopropene) of the [3]radialene were obtained after gradient sublimation according to the procedure described above.
Mp. 197° C.

p) (2E,2'E,2"E)-2,2',2"-(cyclopropane-1,2,3-triylidene)tris(2-(2,6-dichloro-3,5-difluoro-4-(trifluoromethyl)phenyl)-acetonitrile)

(4-trifluoromethyl-2,6-dichloro-3,5-difluorophenyl)acetonitrile (k) was used as starting material. 7.92 g (8.80 mmol; 22% based on tetrachlorocyclopropene) of the [3]radialene were obtained after gradient sublimation according to the procedure described above.
Mp. 220° C.

DOPING EXAMPLES

Example 1

A mixed layer of Spiro-TTB as a host material and (2E, 2'E,2"E)-2,2',2"-(cyclopropane-1,2,3-triylidene)tris(2-(perfluorophenyl)-acetonitrile) (1) as a dopant material have been made by mixed thermal evaporation on a glass substrate in a high vacuum chamber. The doping concentration was 5 mol %, the film thickness 50 nm. The glass substrate has two ITO stripes with a distance of 1 mm as electrodes for the film. From the current-voltage characteristics of the film and the geometry of the sample, the conductivity of the mixed layer was determined to be $1.7 \cdot 10^{-6}$ S/cm.

Example 2

Another film has been made like in example 1. As the dopant, (2E,2'E,2''E)-2,2',2''-(cyclopropane-1,2,3-triylidene)tris(2-(perfluoropyridin-4-yl)-acetonitrile) (m) was used. The conductivity of the film was $4.3 \cdot 10^{-5}$ S/cm.

Example 3

Another film has been made like in example 1. As the dopant, (2E,2'E,2''E)-2,2',2''-(cyclopropane-1,2,3-triylidene)tris(2-(perfluoropyridin-4-yl)-acetonitrile) (m) was used. As the host material, N,N'-Bis(naphthalen-1-yl)-N,N'-bis(phenyl)-benzidine was used. The conductivity of the film was $1.3 \cdot 10^{-5}$ S/cm.

Example 4

Another film has been made like in example 3. As the dopant, (2E,2'E,2''E)-2,2',2''-(cyclopropane-1,2,3-triylidene)tris(2-(4-cyanoperfluorophenyl)-acetonitrile) (n) was used. The doping concentration was 10 mol %. The conductivity of the film was $6.8 \cdot 10^{-5}$ S/cm.

Example 5

Another film has been made like in example 3. As the dopant, (2E,2'E,2''E)-2,2',2''-(cyclopropane-1,2,3-triylidene)tris(2-(2,3,5,6-tetrafluoro-4-(trifluoromethyl)phenyl)-acetonitrile) (o) was used. The doping concentration was 10 mol %. The conductivity of the film was $4 \cdot 10^{-5}$ S/cm.

Example 8

Another film has been made like in example 3. As the dopant, (2E,2'E,2''E)-2,2',2''-(cyclopropane-1,2,3-triylidene)tris(2-(2,6-dichloro-3,5-difluoro-4-(trifluoromethyl)phenyl)-acetonitrile) (p) was used. The doping concentration was 10 mol %. The conductivity of the film was $1.3 \cdot 10^{-5}$ S/cm.

Example 9

Another film has been made like in example 8. As the host, 9,9-Bis[4-(N,N-bis-biphenyl-4-yl-amino)phenyl]-9H-fluorene was used. The conductivity of the film was $1.2 \cdot 10^{-5}$ S/cm. The features of the invention disclosed in the previous description and in the claims can be essential individually as well as in any combination for the realization of the invention in its various embodiments.

The invention claimed is:

1. An organic semiconductive matrix material doped with an organic mesomeric compound, wherein the mesomeric compound comprises a radialene compound of the formula:

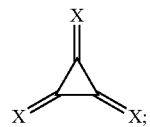

wherein each X is:

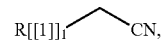

wherein each $R_1$ is selected independently from the group consisting of: aryl and heteroaryl, wherein the aryl and heteroaryl are substituted with at least one electron acceptor group.

2. The matrix material of claim 1, wherein the electron acceptor groups are selected from the group consisting of: cyano, fluoro, trifluoromethyl, chloro, and bromo.

3. The matrix material of claim 1, wherein $R_1$ is selected from the group consisting of: perfluoropyridin-4-yl, tetrafluoro-4-(trifluoromethyl)phenyl, 4-cyanoperfluorophenyl, dichloro-3,5-difluoror-4-(trifluoromethyl)phenyl, and perfluorophenyl.

4. A radialene compound of the formula:

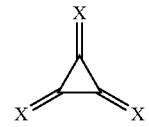

wherein each X is:

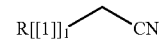

wherein each $R_1$ is selected independently from the group consisting of: aryl and heteroaryl, wherein the aryl and heteroaryl are substituted with at least one electron acceptor group.

5. The radialene compound of claim 4, wherein the compound is: (2E,2'E,2''E)-2,2',2''-(cyclopropane-1,2,3-triylidene)tris(2-(perfluorophenyl)-acetonitrile); (2E,2'E,2''E)-2,2',2''-(cyclopropane-1,2,3-triylidene)tris(2-(perfluoropyridin-4-yl)-acetonitrile); (2E,2'E,2''E)-2,2',2''-(cyclopropane-1,2,3-triylidene)tris(2-(4-cyanoperfluorophenyl)-acetonitrile) (2E,2'E,2''E)-2,2',2''-(cyclopropane-1,2,3-triylidene)tris(2-(2,3,5,6-tetrafluoro-4-(trifluoromethyl)phenyl)-acetonitrile); or (2E,2'E,2''E)-2,2',2''-(cyclopropane-1,2,3-triylidene)tris(2-(2,6-dichloro-3,5-difluoro-4-(trifluoromethyl)phenyl)-acetonitrile).

6. The radialene compound of claim 4, wherein the radialene compound is a radical anionic salt, dianionic salt, or charge transfer complex thereof.

7. Organic semiconductive matrix material of claim 1, wherein the matrix compound is selected from the group consisting of: phthalocyanine copper complex (CuPc); 4,4',4''-tris(N-3-methylphenyl-N-phenyl-amino)triphenylamine (m-MTDATA); 4,4',4''-tris(N-(2-naphthyl)-N-phenylamino)triphenylamine (2-TNATA); MeO-TPD (N,N,N',N'-tetrakis(4-methoxy-phenyl)benzidine); (2,2',7,7'-tetrakis-(N,N-diphenylamino)-9,9'-spirobifluoren (spiro-TTB); N,N'-bis(naphthalen-1-yl)-N,N'-bis(phenyl)-benzidine; N,N'-bis (naphthalen-1-yl)-N,N'-bis(phenyl)-9,9-spiro-bifluorene; 9,9-bis[4-(N,N-bis-biphenyl-4-yl-amino)phenyl]-9H-fluorene; N,N'-bis(phenanthren-9-yl)-N,N'-bis(phenyl)-benzidine; 2,2'-bis[N,N-bis(biphenyl-4-yl)amino]9,9-spiro-bifluorene; 1,3,5-tris{4-[bis(9,9-dimethyl-fluorene-2-yl)amino]phenyl}benzene; and tri(terphenyl-4-yl)amine.

8. Organic semiconductive matrix material of claim 1, wherein the molar doping ratio of doping agent to matrix molecule and/or the doping ratio of doping agent to monomeric units of a polymeric matrix molecule is between about 1:1 and about 1:100,000.

9. An electronic component comprising an electronically functionally active area, wherein the electronically functionally active area comprises one or more radialene compounds of the formula:

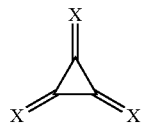

wherein each X is:

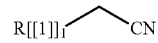

wherein each $R_1$ is selected independently from the group consisting of: aryl and heteroaryl, wherein the aryl and heteroaryl are substituted with at least one electron acceptor group.

10. The electronic component of claim 9, wherein the electronically functionally active area comprises an organic semiconductive matrix material that is doped with at least one doping agent for changing the electronic properties of the semiconductive matrix material, wherein the doping agent comprises one or more of the radialene compounds.

11. The electronic component of claim 9, wherein the electronic component is an organic light-emitting diode, a photovoltaic cell, an organic solar cell, an organic diode or an organic field effect transistor.

* * * * *

UNITED STATES PATENT AND TRADEMARK OFFICE
CERTIFICATE OF CORRECTION

PATENT NO. : 8,057,712 B2
APPLICATION NO. : 12/264511
DATED : November 15, 2011
INVENTOR(S) : Olaf Zeika et al.

It is certified that error appears in the above-identified patent and that said Letters Patent is hereby corrected as shown below:

At column 12, line 10, delete "  " and insert -- 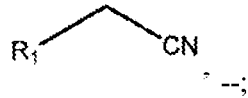 --;

at line 40, delete " 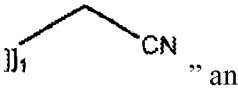 " and insert -- 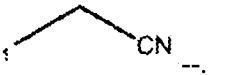 --.

At column 14, line 5, delete "  " and insert -- 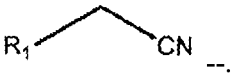 --.

Signed and Sealed this
Third Day of January, 2012

David J. Kappos
*Director of the United States Patent and Trademark Office*